United States Patent
Porscha

(12) 
(10) Patent No.: US 6,252,125 B1
(45) Date of Patent: Jun. 26, 2001

(54) PROCESS AND UNIT FOR THE PRODUCTION OF 1,2-DICHLOROETHANE

(75) Inventor: Peter Porscha, Kelkheim (DE)

(73) Assignee: Krupp Uhde GmbH, Dortmund (DE)

( * ) Notice: Subject to any disclaimer, the term of this patent is extended or adjusted under 35 U.S.C. 154(b) by 0 days.

(21) Appl. No.: 09/549,682

(22) Filed: Apr. 14, 2000

(30) Foreign Application Priority Data

Apr. 14, 1999 (DE) .............................................. 199 16 753

(51) Int. Cl.⁷ .................................................... C07C 17/02
(52) U.S. Cl. .............................................................. 570/246
(58) Field of Search ............................................... 570/246

(56) References Cited

FOREIGN PATENT DOCUMENTS 4131576   3/1993   (DE) .

Primary Examiner—Alan Siegel
(74) Attorney, Agent, or Firm—Roseman & Colin, LLP

(57) ABSTRACT

By a process for the production of 1,2-dichloroethane (EDC) by reaction of ethylene with chlorine in the liquid phase (direct chlorination), the heavy ends being separated from the obtained 1,2-dichloroethane in a heavy-ends column and in a downstream vacuum column and, for the purpose of heat recovery and heating of the column bottoms, a 1,2-dichloroethane part-stream from the direct chlorination passing through a heat exchanger (one attributed to each column) for indirect heat exchange with the bottom product of each column, the aim of the invention is to provide a solution in which the reaction enthalpy of the direct chlorination can be used in a variable manner, thus precluding the above-described disadvantages.

This is achieved by using at least one falling-film evaporator for heating the column bottoms, the bottom product of the respective column being routed to the distributor at the head of the column.

3 Claims, 1 Drawing Sheet

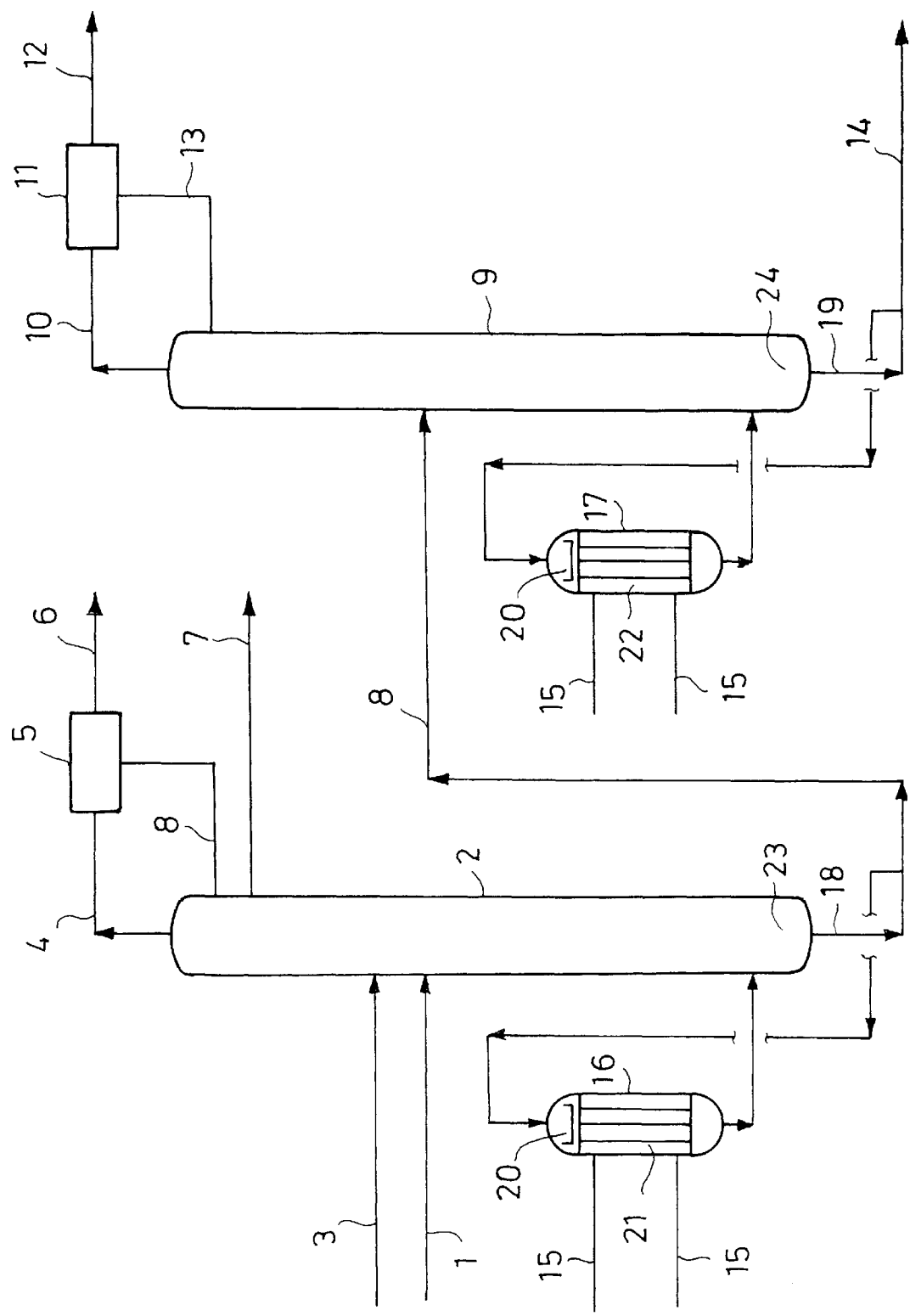

PROCESS AND UNIT FOR THE PRODUCTION OF 1,2-DICHLOROETHANE

BACKGROUND

The invention relates to a process for the production of 1,2-dichloroethane (EDC) by reaction of ethylene with chlorine in the liquid phase (direct chlorination), the heavy ends being separated from the obtained 1,2-dichloroethane in a heavy-ends column and in a downstream vacuum column and, for the purpose of heat recovery and heating of the column bottoms, a 1,2-dichloroethane part-stream from the direct chlorination passing through a heat exchanger (one attributed to each column) for indirect heat exchange with the bottom product of each column. The invention also relates to a unit for running such a process comprising a direct chlorination reactor, a downstream heavy-ends column and a vacuum column downstream of the heavy-ends column, in which one heat exchanger is provided for each column to heat the bottom of the column, a 1,2-dichloroethane part-stream being routed as heating agent from the direct chlorination reactor to the heat exchanger.

The production of vinyl chloride monomer (VCM) from 1,2-dichloroethane (EDC) in the gas phase is achieved by separation of hydrogen chloride (HCl). This gas phase process permits the hydrogen chloride to be separated either catalytically or thermally. In practice, however, the application of the catalytic separation of hydrogen chloride has failed so far because of the short service life of the catalysts. For this reason, it is the thermal separation which is applied, the pure and dry 1,2-dichloroethane being cracked in a pyrolysis furnace at approx. 500° C. to obtain vinyl chloride and hydrogen chloride. The standard ratios of the 1,2-dichloroethane cracking range between 50 and 65%. The unconverted 1,2-dichloroethane from the pyrolysis contains impurities formed in the endothermal separation of the hydrogen chloride. In a subsequent process step, the so-called oxihydrochlorination, the separated hydrogen chloride is converted with the aid of ethylene and oxygen to form 1,2-dichloroethane.

The 1,2-dichloroethane required for the pyrolysis is obtained by the so-called direct chlorination process by means of an exothermal reaction of ethylene and chlorine in liquid 1,2-dichloroethane. A high cooling capacity is required to maintain the reaction temperature.

The 1,2-dichloroethane routed to the pyrolysis furnace requires ultrahigh purity to prevent side reactions which may lead to fouling in the pyrolysis tubes on the one hand and to achieve a high-quality vinyl chloride on the other hand. Hence, the unconverted 1,2-dichloroethane coming from the pyrolysis furnace, the 1,2-dichloroethane from the oxihydrochlorination and, if required, the 1,2-dichloroethane from the direct chlorination are purified in an energy-intensive 1,2-dichloroethane distillation.

In an EDC/VCM plant using this process, the direct chlorination reactor represents one of the major consumers of cooling energy and the column for the heavy-ends separation one of the major consumers of heating energy. Processes with the aim to reduce the energy consumption have already been presented to allow for such economical considerations. In fact, these processes use the reaction heat of the direct chlorination for heating the EDC distillation unit by direct or indirect heating or merely provide for heating energy saving by applying the method of rectification with vapour condensation in the EDC distillation but these processes essentially involve the disadvantages hereinafter described:

It is common practice according to DE 29 35 884 A1 or DE 24 27 045 A1, for example, to pass the product vapours from the direct chlorination reactor to the bottom of the heavy-ends column for direct heating of the latter. This, however, necessitates a very large diameter of the heavy-ends column and a very large surface area for the reflux condenser as several times the amount of each unit of 1,2-dichloroethane newly formed in the direct chlorination is evaporated in the exothermal boiling reaction without forced-air cooling and is additionally rectified in the heavy-ends column together with the other streams of 1,2-dichloroethane. As liquid 1,2-dichloroethane (also several times the amount of the dichloroethane newly formed in the direct chlorination reactor) must at the same time be returned from the bottom of the heavy ends column to the reactor, another disadvantage is that an elevated level of higher boiling by-products is present in the reactor, which has a detrimental effect on the catalyst efficiency on the one hand and which promotes the formation of more by-products on the other hand, finally resulting in a deteriorated yield. For this reason, the reaction heat obtained in the direct chlorination is also unsuitable for the direct heating of the vacuum column of the EDC distillation since the concentration of heavy ends in the bottom exceeds 90%.

In addition to such direct heating, indirect heating processes are common practice in connection with this process type, in which the column reboiler of the EDC distillation is heated by hot reactor recycle 1,2-dichloroethane or vaporous 1,2-dichloroethane from the direct chlorination reactor. For this purpose, thermo-siphon reboilers are used as heat exchangers in these processes as described, for example, in DE 41 33 810 A1, DE 40 39 960 A1 or EP 0 075 742 B1, which requires that a logarithmic-mean temperature difference of approx. 20 to 25° C. be ensured for the existing 1,2-dichloroethane pattern. This involves the following disadvantages: It is required to run the reaction temperature of the reactor at a relatively high level compared to the bottom temperatures of the EDC distillation columns so as to allow an indirect reaction heat transfer to the thermo-siphon reboilers. This will reduce the chlorine and ethylene yields and stimulate the formation of by-products.

Even at relatively low reaction temperatures, the reaction heat of the reactor can be dissipated via the reboilers of the EDC distillation. In such a case, however, the distillation columns must operate at a vacuum pressure which necessitates an especially large diameter and a large reflux condenser for the heavy-ends column and a higher energy input will be required to maintain the vacuum; this is also detrimental to the process economy.

It is also common practice to employ rectification processes with vapours condensation, in which the head vapours of the heavy-ends column are compressed by means of a compressor and used as heating agent for the bottom of the same column (DE 34 40 685 A1). This means, however, that a compressor with rotating parts is required, a machine characterised by a high purchase price and costs for maintenance and spare parts. Even though steam and cooling water costs are saved for the heavy-ends column, the cost of electric power will rise considerably. Another disadvantage is that the integration of the reaction heat developed in the direct chlorination reactor is disregarded by this configuration.

Hence, the aim of the invention is to provide a solution in which the reaction enthalpy of the direct chlorination can be used in a variable manner, thus precluding the above-described disadvantages.

With regard to the process specified in the preceding paragraphs, the present invention provides for a process design in which at least one falling-film evaporator is used for heating the bottoms of the columns, the bottom products being routed to the distributor at the head of the evaporator.

Falling-film evaporators are commonly used for other applications and characterised by the feature that they can be operated with large but theoretically also with any minor temperature difference. In such a falling-film evaporator, liquid and vapours flow downwards in co-current streams. It is of decisive importance for a trouble-free operation to wetten the heating surfaces evenly and adequately with liquid. The concern that the impurities in the bottom of the EDC column may more or less obstruct the distributor of a falling-film evaporator and thus cause an inconsistent liquid distribution to the heating tubes has fostered the prejudice among experts against the use of falling-film evaporators as bottom heaters in the EDC distillation. In fact, said distribution will produce dry spots, incrustations and consequential clogging of individual tubes in the falling-film evaporator.

The use of a falling-film evaporator operated at minor temperature differences involves another rather surprising advantage as regards the mass transfer. It was found that the separating effect improves at low heat flux densities to such an extent that a larger portion of the readily volatile components of a given heat flow changes into the vapour phase. This is a substantial aspect especially for the operation of the vacuum column, as it reduces the product portion (=EDC) of the bottom discharge stream of the vacuum column. The major part of the bottom discharge stream will consist of heavy ends and is to be disposed in a waste incineration unit.

Contrary to the persistent prejudice, it was also found that the fouling resistance of the heating surfaces of the falling-film evaporators is surprisingly low as compared to the thermo-siphon reboilers. Bottom evaporators employed in industrial applications are usually operated at constant heat flow with given external balance of the separating unit. If the heat transfer coefficient is reduced by the fouling, the system suffers an increase in the logarithmic-mean temperature difference. Hence, the time curve of the heating steam pressure is also indicative of the progressive fouling of the heat transfer surface. The comparison of the fouling resistances of the thermo-siphon reboiler and the falling-film evaporator showed that the time curve can be described as qualitatively identical in both cases, but the absolute figures are lower in the case of the falling-film evaporator.

In addition to these major advantages of the process according to this invention, the invention-specific process also contributes to pollution abatement, as it is possible to recover more 1,2-dichloroethane in the bottom of the vacuum column and to reduce fouling of the heat transfer surfaces of the evaporators. Furthermore, the heat transfer surface feasible with a falling-film evaporator for each process vessel unit is considerably larger than that with the conventional-type evaporators. In the case of large plant capacities hence, the bottom of an EDC column can be heated with just one falling-film evaporator whereas several units are required if a thermo-siphon reboiler is installed. This reduces investment costs and surface area requirements. Another advantage is that the liquid inventory of a falling-film evaporator is smaller than that of a thermo-siphon reboiler, which ensures an instantaneous control behaviour. This constitutes a special advantage as it is possible to minimise residual concentrations of light ends (=EDC) in the bottom discharge stream of the vacuum column.

A further advantageous embodiment of this invention is to operate the direct chlorination at temperatures of 75 to 125° C. and pressures of 0.8 to 3 bar. The max. evaporation pressure in the column-mounted evaporator (falling-film evaporator) will then be only 50 mbar higher than the pressure in the bottom of the column to be heated. In addition, the heat transfer coefficient on the evaporation side is almost independent of the logarithmic-mean temperature difference (at a given bottom pressure in the column to be heated, the difference of the heat transfer coefficient on the evaporation side is below 3% with a logarithmic-mean temperature difference between 3° C. and 25° C.).

The invention also suggests a process unit for running the process to produce 1,2-dichloroethane (EDC) by reaction of ethylene with chlorine in the liquid phase (direct chlorination), the heavy ends being separated from the obtained 1,2-dichloroethane in a heavy-ends column and in a downstream vacuum column and, for the purpose of heat recovery and heating of the column bottoms, a 1,2-dichloroethane part-stream from the direct chlorination passing through a heat exchanger for indirect heat exchange with the bottom product of each column, the feature of which is the use of falling-film evaporators as heat exchangers.

BRIEF DESCRIPTION OF DRAWING

FIG. 1 is a flow diagram illustrating the steps of the process described and claimed herein. The drawing shows only such steps and apparatus components that are essential to describe the invention.

DETAILED DESCRIPTION OF THE INVENTION

In the EDC distillation unit, the EDC from the oxihydrochlorination section and the unconverted EDC from the pyrolysis furnace are treated in an energy-intensive EDC distillation. If required, it is also possible to treat the EDC from the direct chlorination in the EDC distillation.

The EDC from the oxihydrochlorination section is first separated from water and light ends in a dehydration/light-ends column which is not represented in the drawing. The EDC from the said section still contains heavy ends and is therefore piped to heavy-ends column 2 via line 1. Unconverted EDC leaving the pyrolysis furnace which is not represented also contains heavy ends and is also piped to heavy-ends column 2 via line 3. Said streams undergo fractional distillation in heavy-ends column 2.

Purified EDC is drawn off at the head of heavy-ends column 2 via line 4, condensed in heat exchanger 5 and recovered as pure EDC either via line 6 or line 7. The reflux is routed to heavy-ends column 2 via line 8.

The heavy ends concentrate in the bottom of the heavy-ends column. It is possible to intensify the purification of the bottom inventory of heavy-ends column 2 by piping the bottom discharge stream via line 8 to vacuum column 9. Purified EDC is drawn off at the head of vacuum column 9 via line 10, condensed in heat exchanger 11 and recovered as pure EDC via line 12. The reflux is routed to the vacuum column via line 13.

Bottom product 14 discharged from vacuum column 9 consists of heavy ends and a small portion of EDC.

According to an embodiment of the invention, columns 2, 9 are heated as follows:

Either a liquid EDC stream or a vaporous EDC stream leaving the direct chlorination reactor, which is not represented, is supplied as heating agent to and discharged from falling-film evaporator 16 via lines 15 to heat the bottom of heavy-ends column 2, falling-film evaporator being tied in in the same manner to heat the bottom of vacuum column 9. Liquid is piped from the bottom of heavy-ends column 18 and from the bottom of vacuum column 19 to special liquids distributor 20 arranged at the head of falling-film evaporators 16 or 17 and designed to prevent inconsistent liquid distribution due to fouling, dry spots, incrustations and consequential clogging of tubes.

The liquid flows downwards as an evenly distributed film of boiling liquids from the head of the evaporator, through the heating tubes of falling-film evaporators 16, 17, thereby evaporating to some extent. The effective logarithmic-mean temperature difference for the evaporation, which is defined as mean temperature 21 or 22 on the heating side and bottom temperature 23 or 24 of columns 2 or 9, can be selected at random and is not subject to any restrictions applicable for minor temperature differences as in the case of thermosiphon reboilers.

The invention is illustrated in more detail by the following special process examples on the basis of the drawing:

EXAMPLE 1

23.1 t/h (tonnes per hour) unconverted EDC from a pyrolysis furnace not represented in the drawing were supplied via line 3 to heavy-ends column 2 as well as 16.2 t/h EDC from the oxihydrochlorination via line 1. Both flows contained heavy ends and had to undergo fractional distillation.

The bottom temperature of column 2 was 100° C. at a pressure of 1.5 bar, the head temperature was 87° C. at a pressure of 1.2 bar. Column 2 was operated at a reflux ratio of R=0.5.

For heating falling-film evaporator 16, it was supplied, via lines 15, with a liquid EDC stream from a direct chlorination reactor not represented in the drawing. The recycle flow rate was 870 t/h, the supply temperature was 115° C. and the discharge temperature 103°.

EXAMPLE 2

Column 2 was operated under the same conditions as in example 1, this time, however, using a vaporous EDC stream from a direct chlorination reactor (not represented in the drawing) for heating falling-film evaporator 16. The operating conditions of the condensed vaporous EDC in supply line 15 to falling-film evaporator 16 were 108° C. and 1.9 bar and the flow rate totalled 50.5 t/h vaporous EDC.

EXAMPLE 3

2.8 t/h heavy-end containing EDC from vacuum column 9 were supplied via line 8. The bottom temperature of column 9 was 89° C. at a pressure of 0.4 bar, the head temperature was 45° C. at a pressure of 0.26 bar. Column 9 was operated at a reflux ratio of 1.0. Bottom discharge stream 14 of the vacuum column contained 0.3 t/h heavy ends and only 3% EDC. For heating falling-film evaporator 17, it was supplied via lines 15 with vaporous EDC from a non-represented flash vessel of a direct chlorination reactor.

The operating conditions of the condensed vaporous EDC in supply line 15 to falling-film evaporator 17 were 98° C. and 1.6 bar and the flow rate totalled 8.1 t/h vaporous EDC.

The invention is, of course, not limited to the above process examples. Further embodiments are possible without abandoning the basic idea.

What is claimed is:

1. A process for the production of 1,2-dichloroethane (EDC), comprising the steps of:
   (a) reacting ethylene with chlorine in liquid phase (direct chlorination) to yield a mixture comprising 1,2-dichloroethane and one or more heavy-end impurities or reaction by-products having boiling points higher than 1,2-dichloroethane;
   (b) separating said heavy-end impurities and by-products from the 1,2-dichloroethane by fractional distillation in a heavy-ends column said column having a top and a bottom;
   (c) removing the concentrated heavy-ends residue from the bottom of said fractional distillation column and feeding it to a vacuum column, wherein residual 1,2-dichloroethane is removed from the heavy-ends residue; and
   (d) passing one or more partial streams of 1,2-dichloroethane from the direct chlorination reactor through a heat exchanger for indirect heat exchange with the bottoms of the fractional distillation column and the vacuum column.

2. Process according to claim 1, characterised in that the direct chlorination is operated at a temperature of 75 to 125° C. and a pressure of 0.8 to 3 bar.

3. The process of claim 1, wherein the indirect heat exchange is performed in one or more falling-film evaporators, each of said evaporators having a top liquid distributor and a bottom outlet, further comprising the steps of:

feeding product streams from the bottoms of the fractional distillation column and vacuum column, respectively, into the top liquid distributor of one or more of said falling-film evaporators;

removing said heated products stream from the bottom outlet;

and returning said heated bottom products to the bottoms of the fractional distillation and vacuum columns; respectively.

* * * * *